(12) United States Patent
Zang et al.

(10) Patent No.: US 12,721,626 B2
(45) Date of Patent: Sep. 1, 2026

(54) STAPLE HEAD AND SURGICAL STAPLER

(71) Applicant: TOUCHSTONE INTERNATIONAL MEDICAL SCIENCE CO., LTD., Suzhou (CN)

(72) Inventors: Hua Zang, Suzhou (CN); Yanping Ye, Suzhou (CN); Kaifen Fu, Suzhou (CN); Yujin Miao, Suzhou (CN)

(73) Assignee: TOUCHSTONE INTERNATIONAL MEDICAL SCIENCE CO., LTD., Suzhou (CN)

( * ) Notice: Subject to any disclaimer, the term of this patent is extended or adjusted under 35 U.S.C. 154(b) by 0 days.

(21) Appl. No.: 19/218,822

(22) Filed: May 27, 2025

(65) Prior Publication Data

US 2025/0281179 A1 Sep. 11, 2025

Related U.S. Application Data

(63) Continuation of application No. PCT/CN2023/134235, filed on Nov. 27, 2023.

(30) Foreign Application Priority Data

Dec. 8, 2022 (CN) ......................... 202211570672.7
Dec. 8, 2022 (CN) ......................... 202223294093.2

(51) Int. Cl.
*A61B 17/00* (2006.01)
*A61B 17/072* (2006.01)
*A61B 90/00* (2016.01)

(52) U.S. Cl.
CPC ........ *A61B 17/07207* (2013.01); *A61B 90/03* (2016.02); *A61B 2017/00477* (2013.01); *A61B 2017/00592* (2013.01); *A61B 2017/07214* (2013.01); *A61B 2017/07285* (2013.01); *A61B 2090/035* (2016.02)

(58) Field of Classification Search
CPC .............. A61B 17/07207; A61B 90/03; A61B 2090/035; A61B 2017/00477; A61B 2017/00592; A61B 2017/07214; A61B 2017/07285; A61B 17/1155; A61B 17/072
USPC ......... 227/175.1, 175.2, 180.1, 176.1, 177.1, 227/179.1
See application file for complete search history.

(56) References Cited

U.S. PATENT DOCUMENTS

2017/0325813 A1* 11/2017 Aranyi ............. A61B 17/07207
2019/0059899 A1* 2/2019 Cappola ............... A61B 17/105

* cited by examiner

*Primary Examiner* — Jacob A Smith
(74) *Attorney, Agent, or Firm* — Westbridge IP LLC

(57) ABSTRACT

A staple head includes a first jaw and a second jaw, a connecting member, a stop member and a firing mechanism. The connecting member is connected to proximal ends of the first jaw and the second jaw. The stop member is rotatably mounted on the connecting member and includes a first blocking portion. The firing mechanism is movable along an axial direction of the stapler and includes a second blocking portion. In a first state, the first blocking portion is located on a path where the second blocking portion moves in a direction toward a distal end side. When an external force is applied to the stop member, the stop member rotates relative to the connecting member in a first direction such that the first blocking portion moves in a direction away from an axial center of the stapler, the stop member enters a second state.

20 Claims, 9 Drawing Sheets

STAPLE HEAD AND SURGICAL STAPLER

CROSS-REFERENCE TO RELATED APPLICATIONS

The present application is a continuation application of International Application No. PCT/CN2023/134235, filed on Nov. 27, 2023. International Application No. PCT/CN2023/134235 claims priority to Chinese Application No. 202211570672.7, filed on Dec. 8, 2022, and Chinese Application No. 202223294093.2, filed on Dec. 8, 2022. All of the aforementioned applications are hereby incorporated by reference in their entireties

TECHNICAL FIELD

The present application relates to the field of medical instruments technologies, and in particular, to a staple head portion and a surgical stapler.

BACKGROUND

In the conventional technologies, a surgical stapler includes a stapler body, an operating handle movably connected to the stapler body, and a staple head portion cooperating with the body. A transmission mechanism is disposed inside the stapler body. The staple head portion includes a staple cartridge assembly and a staple anvil assembly arranged opposite to each other, and a cutter movable within the staple head portion. A firing block is provided inside the staple cartridge assembly. During surgery, a tissue is placed between the nail anvil assembly and the staple cartridge assembly, and a distance between the staple anvil assembly and the staple cartridge assembly is adjusted to gradually clamp the tissue. The operating handle is then held to make the transmission mechanism drive the cutter to move in a direction toward a distal end side, then the cutter propels the firing block to move to make a staple be ejected and formed on a staple anvil while cutting the tissue simultaneously, and thus anastomosis and cutting of the tissue is completed.

For conventional staplers, after one time of firing is completed, all staples in a staple cartridge have been stapled into the tissue, so that the staple cartridge is required to be replaced before the next firing. Before replacing the staple cartridge, if a surgeon, due to inexperience or carelessness, holds the operating handle again, the cutter will be driven to move in the direction toward the distal end side once more through the transmission mechanism, thereby resulting in the tissue being cut without being stapled, and thus leading to surgical failure.

SUMMARY

In view of the problem in the conventional technologies, a purpose of the present application is to provide a staple head portion and a surgical stapler. When a stopper is in a first state, it blocks movement of a firing mechanism in a direction toward a distal end side, so that accidental firing of the stapler is effectively avoided. Meanwhile, when the stopper is in a second state, it does not obstruct the movement of the firing mechanism, so that normal firing of the stapler is allowed.

An embodiment of the present application provides a staple head portion, including:

- a first forceps holder and a second forceps holder arranged opposite to each other;
- a connecting member that is connected to proximal end side of the first forceps holder and the second forceps holder, the first forceps holder being rotatable relative to the connecting member;
- a stopper rotatably mounted on the connecting member and including a first stop portion; and
- a firing mechanism, movable along an axial direction of the surgical stapler and including a second stop portion; where
- the firing mechanism can be driven to move in a direction toward the distal end side, such that the first forceps holder rotates to be relatively closed with the second forceps holder; when the stopper is in a first state, the first stop portion is located on a path that the second stop portion moves in a direction toward a distal end side; and when the stopper is subjected to an external force of a driving member disposed on the first forceps holder to rotate relative to the connecting member in a first direction such that the first stop portion moves away from a axial center direction of the stapler, the stopper enters a second state, and the first stop portion disengages from the path that the second stop portion moves in the direction toward the distal end side, after the staple head portion is closed and the stopper enters the second state, the firing mechanism can be driven to continue moving in the direction toward the distal end side, so the normal firing of the surgical stapler is achieved.

In some embodiments, a distal end of the connecting member is provided with a mounting portion for mounting the stopper; when the first forceps holder and the second forceps holder are in an open state, the mounting portion is at least partially located on a side of the second stop portion away from an axial center of the stapler; and the first stop portion and the second stop portion are provided with a first distance in the axial direction of the surgical stapler.

In some embodiments, the stopper also includes a pivoting portion rotatably mounted on the mounting portion via a pin shaft; and when the stopper is in the first state, the first stop portion protrudes toward the axial center direction of the stapler relative to the pivoting portion.

In some embodiments, the staple head portion also includes the driving member is movable along the axial direction of the stapler. When the driving member is located at the proximal end side of the first forceps holder and the first forceps holder rotates to be relatively closed with the second forceps holder, the driving member abuts against the stopper and drives the stopper to enter the second state from the first state.

In some embodiments, when the stopper enters the second state from the first state, the firing mechanism moves a second distance in the direction toward the distal end side, and the first distance is greater than or equal to the second distance.

In some embodiments, a first driving portion is provided on a proximal end side of the driving member, and a second driving portion cooperating with the first driving portion is provided on a side of the stopper facing toward the axial center of the stapler.

In some embodiments, two opposite sides of the first driving portion and the second driving portion are provided with a first guiding surface and a second guiding surface respectively.

In some embodiments, the first stop portion and the second driving portion are integrally formed; and when the stopper is in the first state, a side of the first stop portion facing toward the first forceps holder is the second guiding surface.

In some embodiments, the firing mechanism includes a cutter and a cutter push rod, a distal end of the cutter is provided with the second stop portion, and a proximal end of the cutter is connected to the cutter push rod.

In some embodiments, when the stopper is in the second state and the firing mechanism moves in the direction toward the distal end side, the stopper at least partially abuts against a side surface of the cutter push rod to be maintained in the second state.

In some embodiments, the staple head portion also includes an elastic member configured to apply a biasing force to the stopper to make the stopper rotate in a second direction opposite to the first direction.

In some embodiments, the mounting portion is provided with a mounting groove opening toward the axial center direction of the stapler, and the stopper at least partially extends into the mounting groove.

In some embodiments, the elastic member is a torsion spring disposed at the pin shaft or a compression spring disposed between the stopper and an inner wall of the mounting groove.

In some embodiments, the connecting member includes a first limiting portion, and the stopper is provided with a second limiting portion; and the first limiting portion cooperates with the second limiting portion to limit a rotation angle of the connecting member in the second direction; and/or, the connecting member also includes a third limiting portion, and the stopper includes a fourth limiting portion; and the third limiting portion cooperates with the fourth limiting portion to limit a rotation angle of the connecting member in the first direction.

In some embodiments, a compression spring passage is provided inside the mounting groove, the compression spring is movably disposed in the compression spring passage, the compression spring passage is arranged perpendicular to a side wall of the firing mechanism, and an axial width of the compression spring passage is greater than an axial width of the mounting groove.

The embodiments of the present application also provide a surgical stapler including the foregoing staple head portion.

The staple head portion and surgical stapler provided in the present application have the following advantages.

By adopting the technical solution provided in the present application, when the stapler satisfies a firing condition, the stopper enters the second state and does not obstruct the movement of the firing mechanism, so that the firing mechanism may be driven to move in the direction toward the distal end side to normally fire the stapler. After firing of the stapler is completed, the stopper enters the first state. By the first stop portion cooperating with the second stop portion, the movement of the firing mechanism in the direction toward the distal end side is effectively blocked, thereby preventing accidental secondary firing of the stapler, and thus surgical effect is effectively improved.

BRIEF DESCRIPTION OF THE DRAWINGS

The other features, purposes, and advantages of the present application will become more apparent through the detailed description of non-limiting embodiments with reference to the following drawings.

DETAILED DESCRIPTION OF THE EMBODIMENTS

Figure 1:
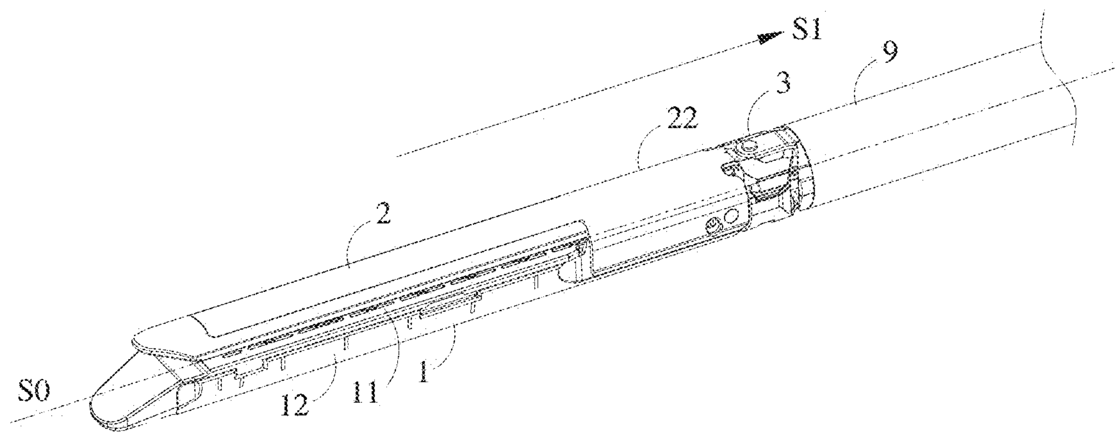
FIG. 1 is a schematic diagram showing cooperation between a staple head portion and a sleeve according to an embodiment of the present application.
Figure 2:
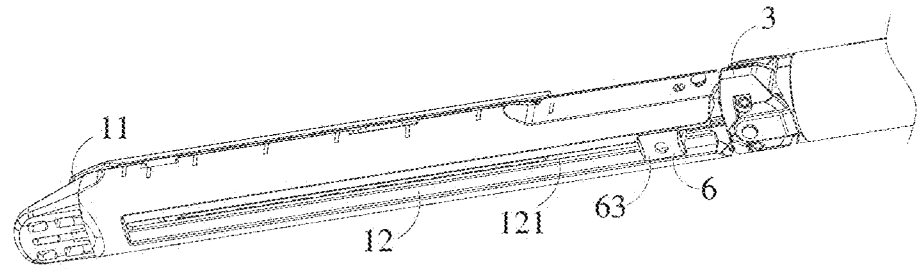
FIG. 2 is a schematic diagram showing cooperation between a staple head portion and a sleeve according to another embodiment of the present application.
Figure 3:
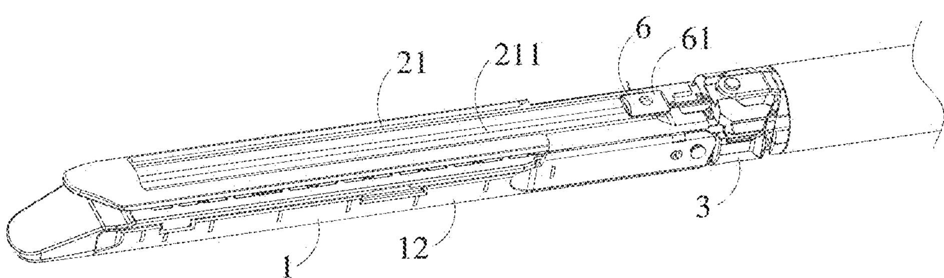
FIG. 3 is a schematic diagram showing cooperation between a staple head portion and a sleeve with a staple anvil housing being omitted according to an embodiment of the present application.
Figure 4:
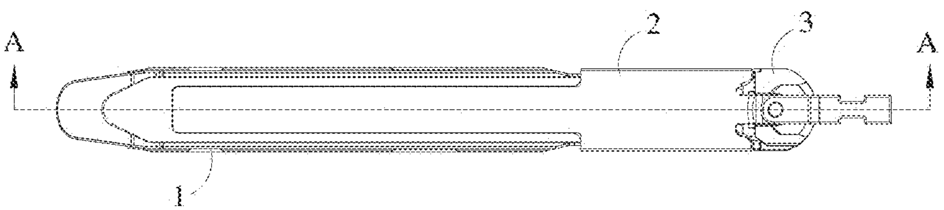
FIG. 4 is a top view of a staple head portion according to an embodiment.

Exemplary embodiments will be described comprehensively with reference to the drawings. It should be understood that, the exemplary embodiments may be implemented in various forms and are not to be construed as being limited to the embodiments set forth herein. On the contrary, these embodiments are provided to make the present application be comprehensive and complete, and to fully convey the concepts of the exemplary embodiments to persons skilled in the art. In the drawings, the same reference numerals denote the same or similar structures, and thus redundant descriptions thereof will be omitted. The terms "or" and "either" in the specification may be interpreted to mean either "and" or "or" respectively. Although terms such as "upper," "lower," and "between" may be used in the specification to describe various exemplary features and elements of the present application, such terms are used herein merely for convenience of description based on the orientations shown in the drawings. Nothing in the present specification shall be interpreted as requiring a particular three-dimensional orientation of a structure to fall within the scope of the present application. Although terms such as "first" or "second" is used herein for denoting certain features, such terms are merely used for illustrative purposes and are not to be construed as limiting the quantity and importance of the specific features.

In view of the problem in the related technologies, it is necessary to provide a structure that prevents accidental secondary firing when the staple cartridge has not been replaced after one time of the firing.

The present application provides a staple head portion for a surgical stapler and a surgical stapler including the staple head portion. The surgical stapler includes a stapler body, an operating handle and a staple head portion disposed at a distal end of the stapler body. When a firing condition of the stapler is satisfied, holding the operating handle for firing to make an actuation force be transmitted to the staple head portion through a transmission mechanism inside the stapler body, and thereby enabling the staple head portion to complete anastomosis and cutting operations of a tissue. The staple head portion includes a first forceps holder and a second forceps holder arranged opposite to each other, a connecting member, a stopper and a firing mechanism. The connecting member is connected to proximal end sides of the first forceps holder and the second forceps holder. The stopper is rotatably mounted on the connecting member and includes a first stop portion. The firing mechanism is movable along an axial direction of the stapler and includes a second stop portion.

When the stopper is in a first state, the first stop portion is located on a path that the second stop portion moves in a direction toward a distal end side, so that movement of the firing mechanism in the direction toward the distal end side is blocked, thereby the stapler cannot be fired, and thus accidental firing of the stapler is effectively avoided. When the stopper is subjected to an external force to rotate relative to the connecting member in a first direction such that the first stop portion moves in a direction away from an axial center direction of the stapler, the stopper enters a second state to make the first stop portion disengage from the path that the second stop portion moves in the direction toward the distal end side. In this point, the firing mechanism is driven to move in the direction toward the distal end side, and thereby normally firing the stapler.

Structures of staple head portions in each specific embodiment of the present application are described in detail below with reference to the drawings. It may be understood that, the specific embodiments are not intended to limit the scope of protection of the present application.

FIG. 1 to FIG. 17 show a structure of a staple head portion according to a first embodiment of the present application. As shown in FIG. 1 to FIG. 5, the staple head portion includes a first forceps holder and a second forceps holder arranged opposite to each other, and a connecting member 3. The staple head portion is disposed on a distal end of a sleeve 9 of a stapler body. A jaw is formed between the first forceps holder and the second forceps holder, in general, one of the first forceps holder and the second forceps holder is in a fixed state, and the other may be in a relatively open state and a relatively closed state relative to the fixed forceps holder. In this embodiment, take the second forceps holder serving as the fixed forceps holder, the first forceps holder being movable, the first forceps holder being provided with a staple cartridge assembly 1, and the second forceps holder being a staple anvil assembly 2 as an example for description. The staple cartridge assembly 1 includes a staple cartridge frame 12 and a staple cartridge 11 for accommodating staples therein. The staple anvil assembly 2 includes a staple anvil housing 22 and a staple anvil body 21. Proximal end sides of the staple cartridge assembly 1 and the staple anvil assembly 2 are connected to the connecting member 3, and the staple cartridge assembly 1 is rotatable relative to the connecting member 3, so that the staple cartridge assembly 1 has an open state and a closed state relative to the staple anvil assembly 2, that is, the staple head portion has a jaw open state and a jaw closed state.

Figure 5:
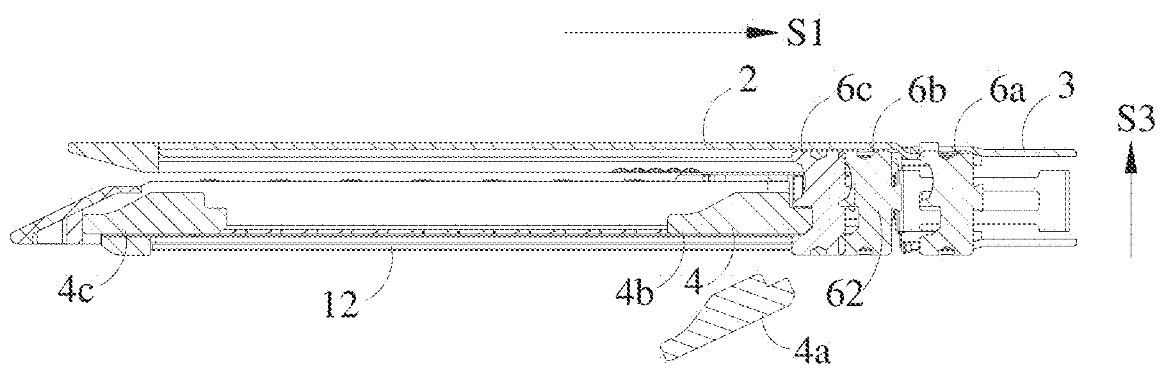
FIG. 5 is a cross-sectional view taken along a line A-A in FIG. 4.
Figure 11:
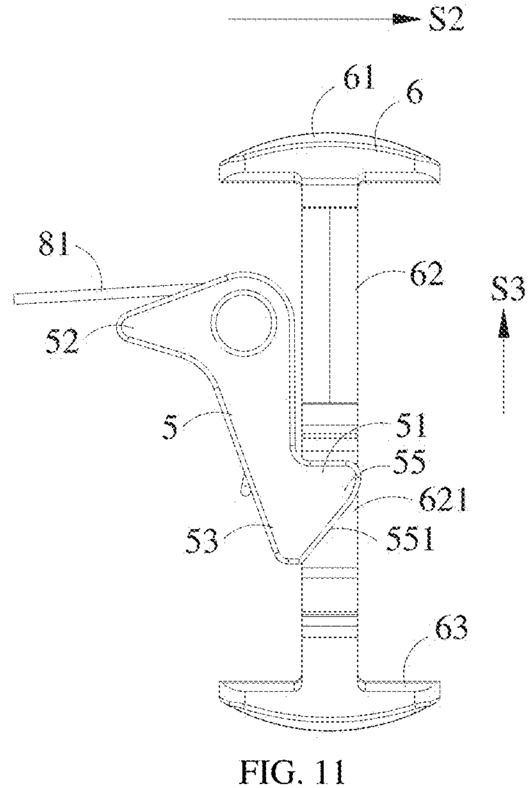
FIG. 11 is a schematic diagram showing cooperation between a stopper and a cutter when the stopper is in the first state according to an embodiment of the present application.

In the present application, a distal end side and a proximal end side are defined relative to an operator, the proximal end side refers to a side closer to the operator, and the distal end side refers to a side farther from the operator, that is, a side closer to a surgical position is a distal end side. A direction along an axial center of the stapler is defined as an axial direction, that is, a direction from a distal end side to a proximal end side of the stapler, or a direction from the proximal end side to the distal end side of the stapler. A direction S1 in FIG. 1 is defined as the direction from the distal end side to the proximal end side of the stapler, the direction S1 or a direction opposite to the direction S1 is the axial direction. In FIG. 5, a direction S3 is a longitudinal direction, that is, a height direction. In FIG. 11, a direction S2 is transverse direction, that is, a width direction. In FIG. 1, a direction S0 is the axial center direction of the stapler. For a component, a side of the component close to an axial center of the stapler is an inner side, and a side away from the axial center of the stapler is an outer side.

The staple head portion also includes a firing mechanism, and the firing mechanism includes a cutter 6 and a cutter push rod 7. A distal end side of the cutter push rod 7 is connected to a proximal end side of the cutter 6, and the cutter push rod 7 may be driven to make the cutter 6 move along an axial direction of the stapler. The cutter 6 includes a first crossbeam 61, a connecting portion 62 and a second crossbeam 63 that are arranged sequentially from top to bottom, and an upper distal end side of the connecting portion 62 is a blade for cutting a tissue. Two ends of the connecting portion 62 enters a first cutter groove 211 of the staple anvil body 21 and a second cutter groove 121 of the staple cartridge frame 12, respectively, and the first crossbeam 61 and the second crossbeam 63 respectively cooperate with the staple anvil body 21 and the staple cartridge frame 12. As shown in FIG. 5, when the cutter 6 is located on the proximal end side, it has three positions 6*a*, 6*b*, and 6*c*. When the staple cartridge assembly 1 is opened relative to the staple anvil assembly 2, the cutter 6 is located at the proximal end side position 6*a* of the nail cartridge assembly 1. By holding the operating handle, the cutter push rod 7 is enabled to drive the cutter 6 to move in the direction toward the distal end side to the position 6*b*, and at this point, the staple cartridge assembly 1 gradually closes relative to the staple anvil assembly 2. After the jaw of the staple head portion is closed, the cutter 6 is driven by the cutter push rod 7 to continue moving in the direction toward the distal end side to a distal end of the staple cartridge assembly 1, and thereby completing the firing of the stapler.

As shown in FIG. 6 to FIG. 11, the staple head portion also includes a stopper 5, the stopper 5 includes a first stop portion 51, and a distal end of the cutter 6 is correspondingly provided with a second stop portion 621. A distal end of the connecting member 3 is provided with a mounting portion 30 for mounting the stopper 5. When the staple cartridge assembly 1 is opened relative to the staple anvil assembly 2, the mounting portion 30 is at least partially located on a side of the second stop portion 621 away from the axial center direction of the stapler, and the mounting portion 30 is at least partially located on a side in a transverse direction of the second stop portion 621. The mounting portion 30 is provided with a mounting groove 31 opening toward the axial center direction of the stapler, and the stopper 5 at least partially extends into the mounting groove 31. The mounting portion 30 is internally provided with a mounting hole 34, the stopper 5 is provided with a pivoting portion 54, and the pivoting portion 54 is rotatably mounted in the mounting hole 34 of the mounting portion 30 via a pin shaft 36.

Figure 10:
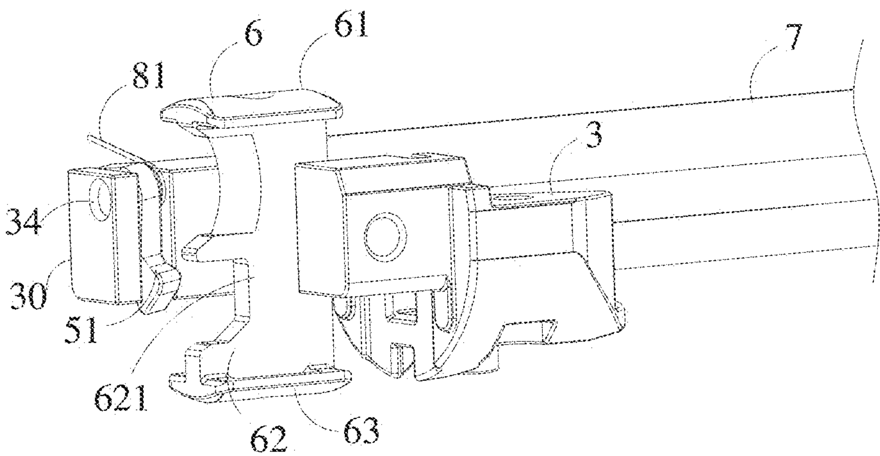
FIG. 10 is a schematic diagram showing cooperation between a stopper in a first state and a firing mechanism according to an embodiment of the present application.
Figures 15, 16:
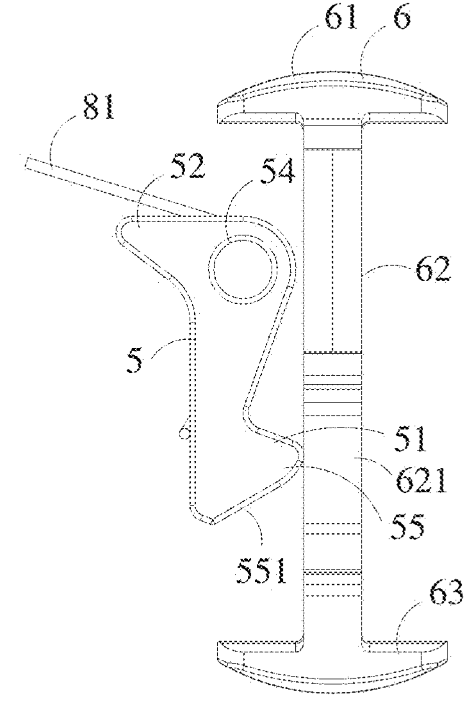
FIG. 15 is a schematic diagram showing cooperation between a stopper and a cutter when the stopper is in a second state according to an embodiment of the present application.
FIG. 16 is a schematic diagram showing cooperation between a stopper and a firing mechanism during a firing process of the stapler according to an embodiment of the present application.

The stopper 5 has a first state and a second state, FIG. 10 and FIG. 11 show cooperation between the stopper 5 in the first state and the cutter 6, and FIG. 15 shows the cooperation between the stopper 5 in the second state and the cutter 6. As shown in FIG. 10 and FIG. 11, when the stopper 5 is in the first state, the first stop portion 51 is located on a path that the second stop portion 621 moves in the direction toward the distal end side, and thereby blocking the movement of the cutter 6 in the direction toward the distal end side, that is, the stapler cannot be fired, and thus accidental firing of the stapler is effectively avoided. As shown in FIG. 15, when the stopper 5 is subjected to an external force and rotates relative to the connecting member 3 in a first direction to make the first stop portion 51 move in a direction away from the axial center direction of the stapler, the stopper 5 enters the second state. In the second state, the first stop portion 51 disengages from the path that the second stop portion 621 moves in the direction toward the distal end side, and at this point, the cutter 6 is driven to move in the direction toward the distal end side, and thus the stapler is normally fired. From the perspective of FIG. 11, the first direction is a clockwise direction.

Figure 6:
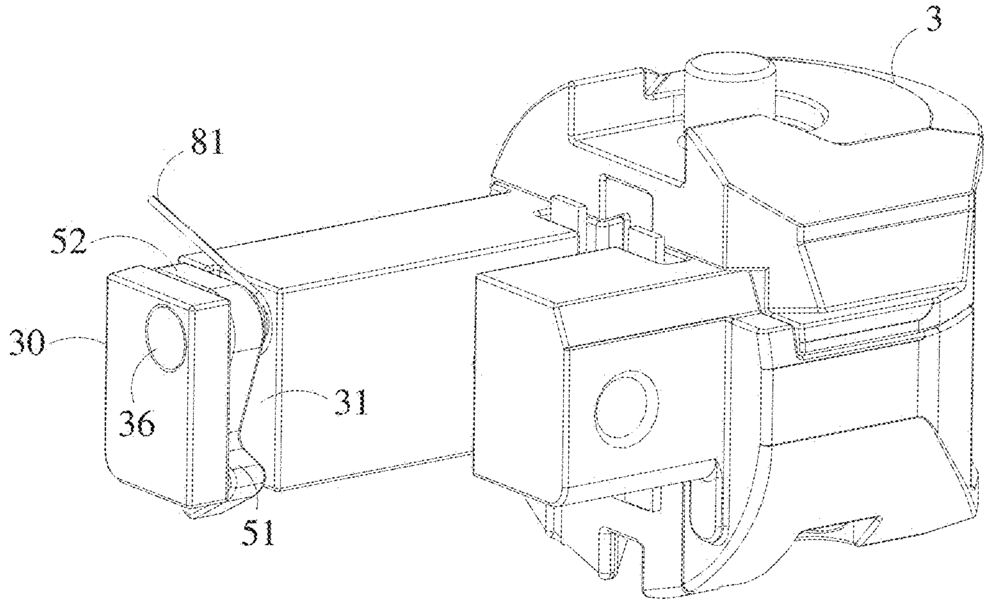
FIG. 6 is a schematic diagram showing cooperation between a connecting member and a stopper according to an embodiment of the present application.
Figure 7:
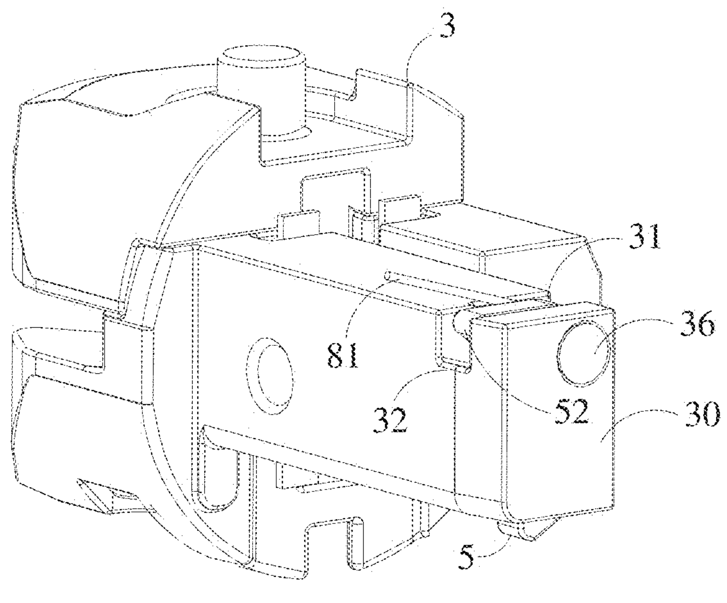
FIG. 7 is a schematic diagram showing cooperation between a connecting member and a stopper according to another embodiment of the present application.
Figure 8:
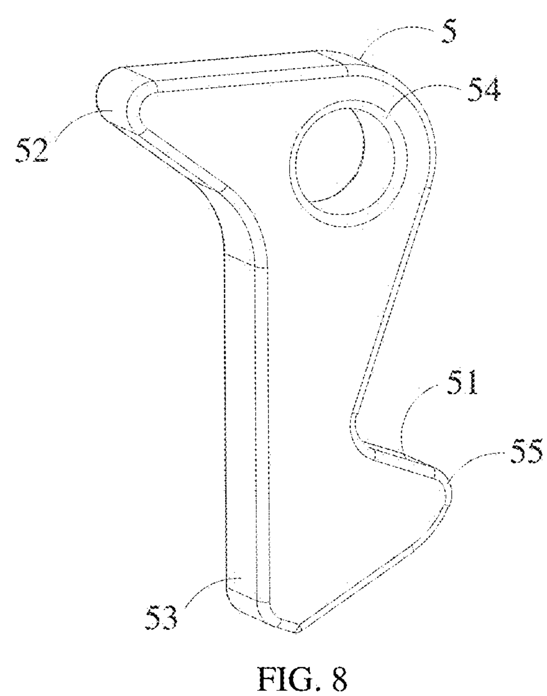
FIG. 8 is a schematic structural diagram of a stopper according to an embodiment of the present application.
Figure 9:
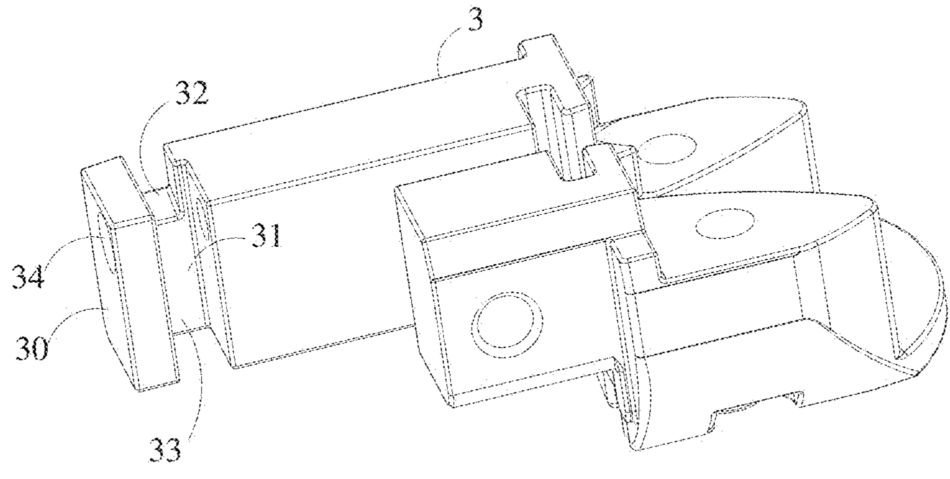
FIG. 9 is a schematic structural diagram of a connecting member according to an embodiment of the present application.

The mounting groove 31 is internally provided with an elastic member that is configured to apply a biasing force to the stopper 5 to rotate the stopper 5 in a second direction, and the second direction is opposite to the first direction. The second direction is a counterclockwise direction from the perspective of FIG. 11. Therefore, when the stopper 5 is not subjected to an external force that drives it to rotate in the first direction, the stopper 5 is maintained in the first state under the action of the elastic member. As shown in FIG. 6, in this embodiment, the elastic member is a torsion spring 81 sleeved on the pin shaft 36. When the stopper 5 is subjected to an external force that drives it to rotate in the first direction to enter the second state, the torsion spring 81 is driven to elastically deform. After the external force acting on the stopper 5 is removed, under the action of the restoring force of the elastic deformation of the torsion spring 81, the stopper 5 rotates in the second direction to return from the second state to the first state.

As shown in FIG. 7 to FIG. 10, the connecting member 3 includes a first limiting portion 32 and a third limiting portion 33, and the stopper 5 is provided with a second limiting portion 52 and a fourth limiting portion 53. Positions of the second limiting portion 52 and the fourth limiting portion 53 are adapted to the first limiting portion 32 and the third limiting portion 33, respectively. The second limiting portion 52 and the fourth limiting portion 53 are respectively located on two sides in a longitudinal direction of the pivoting portion 54, that is, they are located above and below the pivoting portion 54, respectively. The second limiting portion 52 protrudes in a direction away from the axial center direction of the stapler compared with the pivoting portion 54, and the second limiting portion 52 may also serve to reinforce an overall structural strength of the stopper 5. The first limiting portion 32 is a stepped portion that is adapted to a shape of the second limiting portion 52, and an extending direction of an upper surface of the stepped portion intersects with an extending direction of the third limiting portion 33. The first limiting portion 32 cooperates with the second limiting portion 52 to limit a rotation angle of the connecting member 3 in the second direction. When the stopper 5 rotates in the second direction under the action of the torsion spring 81, the first limiting portion 32 limits a rotation stroke of the second limiting portion 52 to prevent a rotation angle of the stopper 5 from being too large. The fourth limiting portion 53 is a side wall of the stopper 5 at a side that away from the axial center of the stapler, and the third limiting portion 33 is an inner wall of the mounting groove 31 at a side that away from the axial center of the stapler. In this embodiment, a surface of the first limiting portion 32 that is opposite to the second limiting portion 52 is substantially perpendicular to the longitudinal direction, and an extending direction of the third limiting portion 33 is substantially parallel to the longitudinal direction. The third limiting portion 33 cooperates with the fourth limiting portion 53 to limit the rotation angle of the stopper 5 in the first direction. When the stopper 5 rotates in the first direction under the action of an external force, the third limiting portion 33 limits a rotation stroke of the fourth limiting portion 53 to prevent the rotation angle of the stopper 5 from being too large. In another alternative embodiment, the mounting portion 30 of the connecting member 3 may not be provided with the mounting groove 31, but instead, the stopper 5 is rotatably mounted on the stopper 5 on either a side surface or a distal end surface of the mounting portion 30 directly, which also falls within the scope of protection of the present application.

In this embodiment, the switching of the stopper 5 from the first state to the second state is driven by a driving member 4. The driving member 4 is a firing block disposed on the staple cartridge assembly 1. A first driving portion 41 is provided on a proximal end side of the driving member 4, and a side of the stopper 5 facing toward the axial center of the stapler is provided with a second driving portion 51 cooperating with the first driving portion 41. A first guiding surface 411 and a second guiding surface 551 are provided on two opposite sides of the first driving portion 41 and the second driving portion 55, respectively. The first guiding surface 411 is an inclined surface located above the first driving portion 41. In this embodiment, the first stop portion 51 and the second driving portion 55 are integrally formed, that is, as shown in FIG. 11, a protruding block that protrudes toward the cutter 6 serves as both the first stop portion 51 and the second driving portion 55. When the stopper 5 is in the first state, a side of the first stop portion 51 facing toward the staple cartridge assembly 1 is the second guiding surface 551, and at this point, the second guiding surface 551 is inclined relative to both the longitudinal direction and the axial direction.

As shown in FIG. 5 and FIG. 12 to FIG. 15, when the staple cartridge assembly 1 is opened relative to the staple anvil assembly 2, the driving member 4 is located on the proximal end side of the staple cartridge assembly 1, but because the staple cartridge assembly 1 is located at a position away from the staple anvil assembly 2, the driving member 4 is located at the position 4*a* in FIG. 5, so that the driving member 4 will not contact with the stopper 5, and thus the stopper 5 is in the first state under the action of the torsion spring 81. The cutter 6 is located at the position 6*a* on the proximal end side of the stopper 5, and there is a first axial distance between the second stop portion 621 of the cutter 6 and the first stop portion 51 of the stopper 5. When the cutter 6 moves a second distance in the direction toward the distal end side to the position 6*b*, the staple cartridge assembly 1 gradually approaches the staple anvil assembly 2 to close the jaw, and the driving member 4 moves with the staple cartridge assembly 1 to the position 4*b*. Since the first distance is greater than the second distance, a distance between the proximal end side of the driving member 4 and the distal side of the cutter 6 is a third distance in the axial direction at this point. The third distance is the distance between the position 4*b* and the position 6*b*, which is substantially equal to the first distance minus the second distance. In an alternative embodiment, the second distance may also be equal the first distance, at this time the proximal end side of the driving member 4 abuts against the distal side of the cutter 6. As the driving member 4 moves from the position 4*a* to the position 4*b*, the first driving portion 41 of the driving member 4 moves toward the stopper 5 until it abuts against the second driving portion 55, and drives the stopper 5 to rotate in the first direction, so that the first stop portion 51 moves in a direction away from the axial center of the stapler, and thus making the stopper 5 enter the second state.

The working principle of the stopper 5 in different states is specifically described below with reference to FIG. 5 and FIG. 10 to FIG. 17.

When the staple cartridge assembly 1 is opened relative to the staple anvil assembly 2, the driving member 4 is located at the position 4*a* on the proximal side of the staple cartridge assembly 1, so that it will not contact with the stopper 5. The cutter 6 is located at the position 6*a* on the proximal end side of the staple cartridge assembly 1. As shown in FIG. 10 and FIG. 11, the stopper 5 is not subjected to an acting force from the driving member 4, under the action of the torsion spring 81, the stopper 5 is maintained in the first state, and the first stop portion 51 is located on the path that the second stop portion 621 moves in the direction toward the distal end side. The cutter 6 is located on the proximal end side of the stopper 5, and there is the first distance between the second stop portion 621 and the first stop portion 51 of the stopper 5 in the axial direction.

Figure 12:
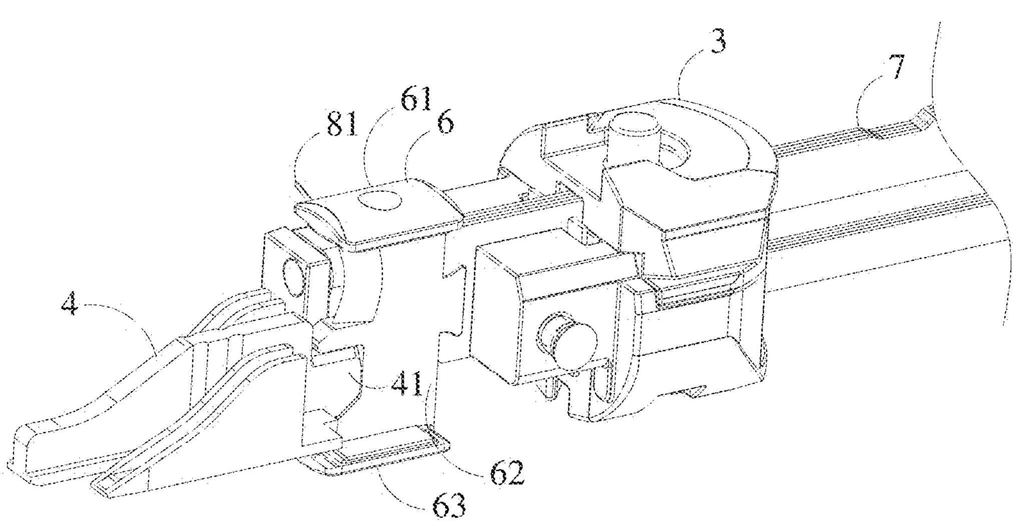
FIG. 12 is a schematic diagram showing cooperation between a stopper and a firing mechanism after a stapler is closed according to an embodiment of the present application.
Figure 13:
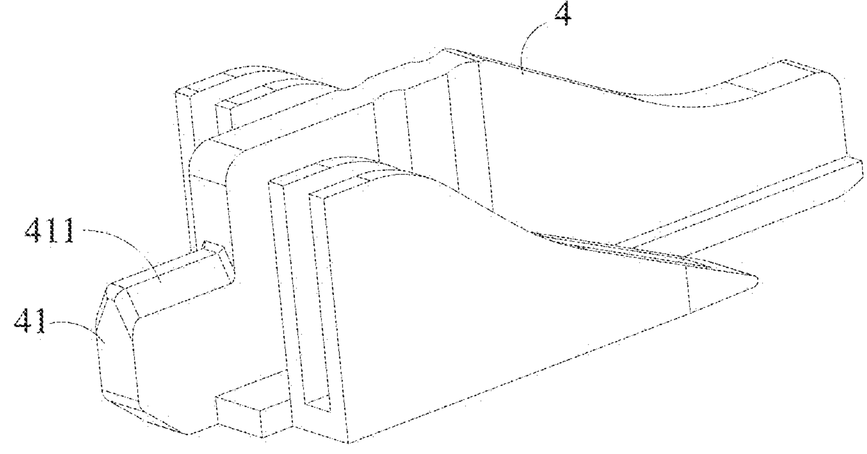
FIG. 13 is a schematic structural diagram of a driving member according to an embodiment of the present application.
Figure 14:
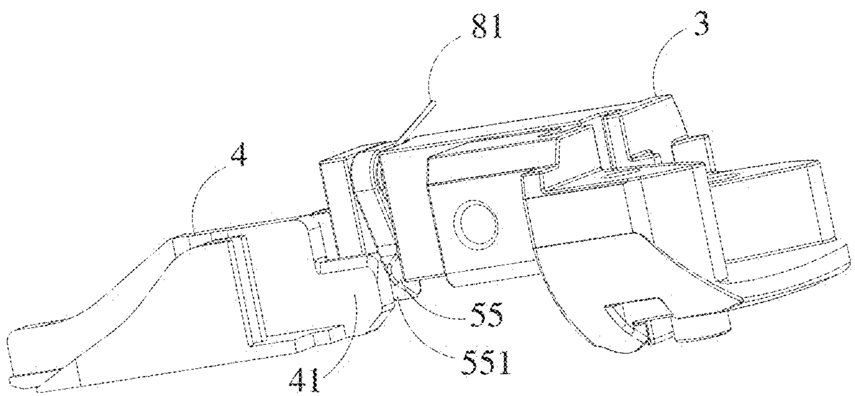
FIG. 14 is a schematic diagram showing cooperation between a driving member and a stopper according to an embodiment of the present application.

When the staple head portion is placed in a surgical position, the jaw is required to be closed to clamp the tissue. At this point, by holding the operating handle, the transmission mechanism drives the cutter push rod 7 and the cutter 6 to move the second distance in the direction toward the distal end side to the position 6*b*, the staple cartridge assembly 1 gradually approaches the staple anvil assembly 2 to close the jaw, and the driving member 4 moves with the staple cartridge assembly 1 to the position 4*b*. In this state, there is the third distance between the proximal end side of the driving member 4 and the distal side of the cutter 6. As shown in FIG. 12 and FIG. 14, during a closing process of the jaw, the first driving portion 41 of the driving member 4 abuts against the second driving portion 55 of the stopper 5 to drive the stopper 5 to rotate in the first direction, so that the first stop portion 51 moves toward the direction away from the axial center of the stapler, that is, it moves toward an outer side of the cutter 6, and then the stopper 5 moves to the second state shown in FIG. 15. During this process, the torsion spring 81 is compressed to generate elastic deformation, and the first stop portion 51 disengages from the path that the second stop portion 621 moves in the direction toward the distal end side.

After the staple head portion is closed and the stopper 5 enters the second state, the operating handle is held again, so that the cutter push rod 7 and the cutter 6 is driven by the transmission mechanism to continue moving in the direction toward the distal end side. The cutter 6 firstly moves to the position 6*c* to abut against the proximal end side of the driving member 4, and then drives the driving member 4 located at the position 4*b* to move in the direction toward the distal end side to the position 4*c* to push the staple out to suture the tissue, and the cutter 6 cuts the tissue, so that normal firing of the stapler is achieved. In the firing process of the stapler, the driving member 4 moves in the direction toward the distal end side to make the first driving portion 41 disengage from the second driving portion 55, and the first stopping portion 51 of the stopper 5 abuts against the side wall of the connecting portion 62 of the cutter 6 such that the stopper 5 is maintained in the second state. After the cutter 6 completely moves to the distal end side of the stopper 5, as shown in FIG. 16, the first stopping portion 51 of the first stop portion 51 abuts against a side surface of the cutter push rod 7 to maintained the stopper 5 in the second state, and the torsion spring 81 is maintained in a state with an elastic deformation amount.

Figure 17:
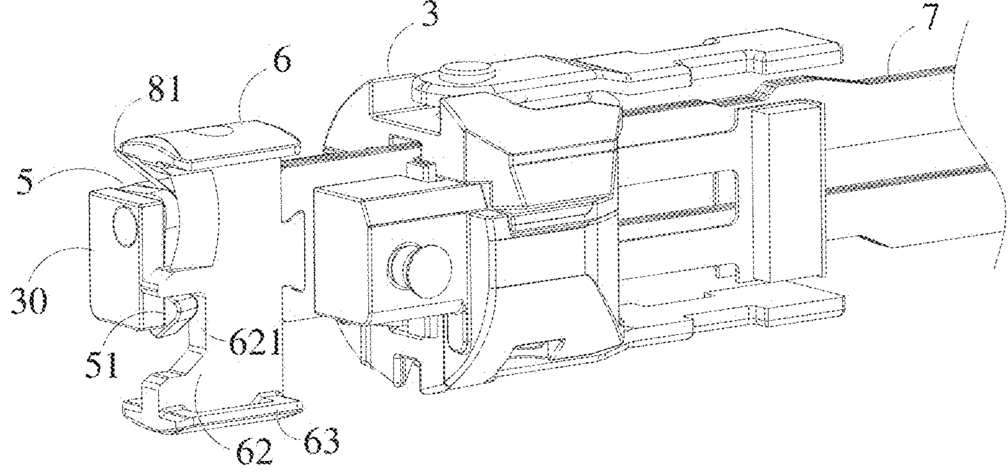
FIG. 17 is a schematic diagram showing cooperation between a stopper and a firing mechanism after the stapler is fired according to an embodiment of the present application.

After the firing of the stapler is completed, under the holding action of the cutter push rod 7, the stopper 5 is still in the second state, at this time, the cutter 6 and the cutter push rod 7 are driven by the reset mechanism to reset in a direction towards the proximal end side, while the driving member 4 still remains at the position 4*c*, and will not be reset to the proximal end side of the staple cartridge assembly 1. In the process that the cutter 6 is reset from the distal end side to the proximal end side, the first stop portion 51 of the stopper 5 still abuts against the side wall of the cutter push rod 7, and when the cutter 6 moves to the position where the stopper 5 is located, the first stop portion 51 abuts against the side wall of the connecting portion 62 of the cutter 6 until the cutter 6 is completely reset to the proximal end side of the first stop portion 51. At this point, the first stop portion 51 no longer abuts against the cutter 6 and the cutter push rod 7, and there is no driving force from the driving member 4. Therefore, under the action of the restoring force of the elastic deformation of the torsion spring 81, the stopper 5 rotates in the second direction, so that the first stop portion 51 moves in a direction toward the axial center of the stapler, that is, it moves towards the inner side, thereby the first stop portion 51 enters the path that the second stop portion 621 moves in the direction toward the distal end side again, and thus the stopper 5 enters the first state. At this point, if the operating handle is held to make the cutter 6 move in the direction toward the distal end side to a position where the staple head portion is closed, since there is no driving member 4 at the proximal end side of the staple cartridge assembly 1, so that the stopper 5 is still in the first state. If the operating handle is held to make the cutter 6 move in the direction toward the distal end side, as shown in FIG. 17, the second stop portion 621 of the cutter 6 is blocked by the first stop portion 51 of the stopper 5, thereby the cutter 6 cannot continue moving in the direction toward the distal end side, so that the stapler cannot be fired, and thus secondary accidental firing when the staple cartridge 11 has not been replaced is effectively avoided.

Figure 18:
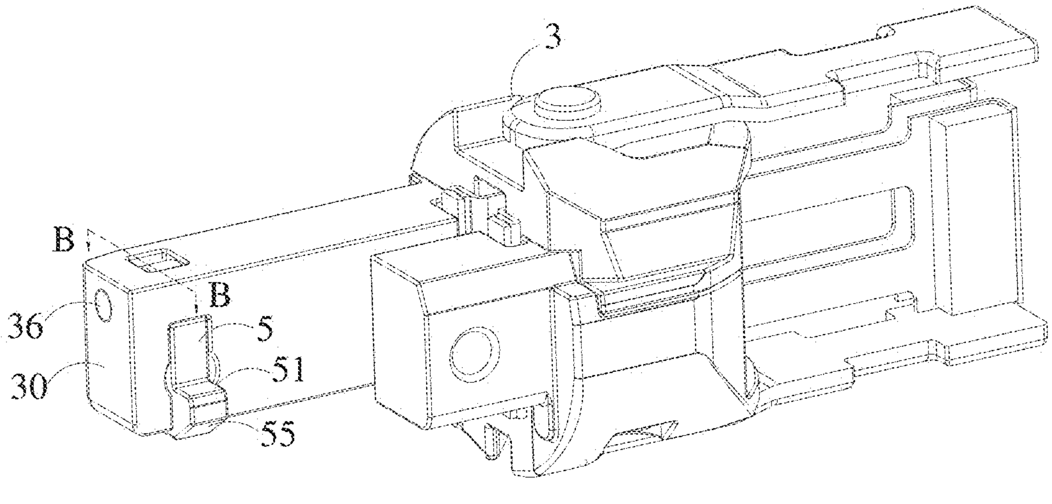
FIG. 18 is a schematic diagram showing cooperation between a stopper and a connecting member according to an embodiment of the present application.
Figure 19:
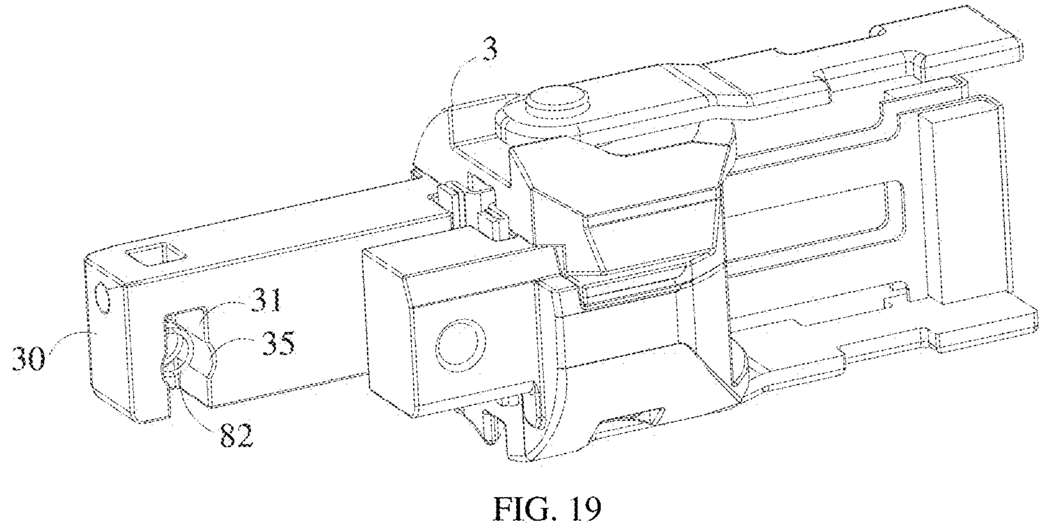
FIG. 19 is a schematic structural diagram of a connecting member according to an embodiment of the present application.
Figure 20:
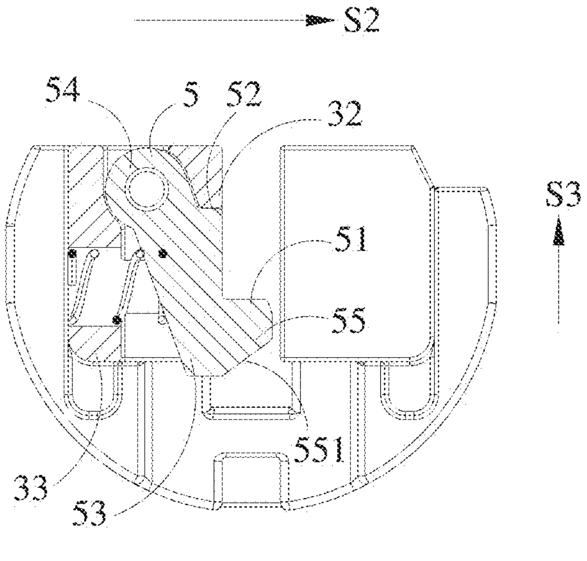
FIG. 20 is a cross-sectional view taken along a line B-B in FIG. 18.

FIG. 18 to FIG. 20 show a structure that the stopper 5 cooperates with connecting member 3 according to a second embodiment of the present application. The difference between this embodiment and the first embodiment lies in that the structure that the connecting member 3 cooperates with the stopper 5 is different, and the structure that the elastic member cooperates with the stopper 5 is different. In this embodiment, the elastic member is a compression spring 82, and a compression spring passage 35 for accommodating the compression spring 82 is disposed inside the mounting groove 31. The compression spring 82 is movably disposed in the compression spring passage 35, and the compression spring passage 35 is arranged perpendicular to a side wall of the cutter 6. An axial width of the compression spring passage 35 is greater than an axial width of the mounting groove 31, so that the compression spring 82 will not fall out from the bottom of the mounting groove 31. Two ends of the compression spring 82 abut against a bottom wall of the compression spring passage 35 and an outer surface of the stopper 5, respectively. The second limiting portion 52 is a protruding portion located above the pivoting portion 54 and protruding toward an inner side relative to the pivoting portion 54, and the first limiting portion 32 is a stepped portion located on a bottom wall of the mounting groove 31 and shaped to match with the second limiting portion 52 to limit the rotation angle of the stopper 5 in the second direction. An upper surface of the stepped portion is substantially perpendicular to the longitudinal direction and intersects with an extending direction of the third limiting portion 33. The second limiting portion 52 may also reinforce the overall structural strength of the stopper 5. The third limiting portion 33 is an inner wall located below the compression spring passage 35, and the fourth limiting portion 53 is a side wall of the mounting groove 31 located below the pivoting portion 54 and located on an outer side of the stopper 5. When the stopper 5 is subjected to an external force to rotate in the first direction to enter the second state, the stopper 5 compresses the compression spring 82 to elastically deform, and the third limiting portion 33 cooperates with the fourth limiting portion 53 to limit the rotation angle of the stopper 5 in the first direction. After the external force acting on the stopper 5 is removed, under the action of a restoring force of the elastic deformation of the compression spring 82, the stopper 5 rotates in the second direction to enter the first state. Other structures in the second embodiment are the same as the corresponding structures in the first embodiment, and will not be described in detail herein again. The structure in the second embodiment may also be combined with the first embodiment, for example, the torsion spring 81 arranged in the mounting groove 31 in the first embodiment is directly replaced with the compression spring 82, the structure of the stopper 5 is kept unchanged, or the matching structure of the mounting groove 31 and the stopper 5 in the first embodiment is replaced with the structure in the second embodiment, while retaining the torsion spring 81 as the elastic member. In this embodiment, the torsion spring 81 in the first embodiment is replaced with the compression spring 82, a gap between the stopper 5 and the connecting member 3 is reduced while increasing the connection strength, and thereby preventing the stopper 5 from wobbling during use.

In the foregoing embodiments, taking the first forceps holder as the staple cartridge assembly and the second forceps holder as the staple anvil assembly as an example for illustrating, the staple anvil assembly is fixed relative to the connecting member, the staple cartridge assembly is rotatable relative to the connecting member, and the driving member is disposed on the staple cartridge assembly. In other alternative embodiments, the first forceps holder may be configured as the staple anvil assembly and the second forceps holder as the staple cartridge assembly, and with the driving member being disposed on the staple anvil assembly. In such construction, the staple cartridge assembly is fixed relative to the connecting member, and the staple anvil assembly is rotatable relative to the connecting member. Before the staple head portion is closed, the driving member in the staple anvil assembly is away from the stopper without abutting against the second driving portion, and when the staple head portion is closed and the driving member is located on the proximal end side of the staple anvil assembly, the driving member abuts against the second driving portion to drive the stopper to enter the second state.

In the foregoing embodiment, taking the first stop portion and the second driving portion being integrally formed as an example for description. In other alternative embodiments, the first stop portion and the second driving portion may also be two components, for example, two protrusions are disposed on an inner side of the stopper, and the second driving portion is located below the first stop portion. When the staple cartridge assembly rotates to gradually close the jaw, the first driving portion firstly abuts against the second driving portion to drive the stopper to rotate in the first direction.

In the above embodiments, two exemplary implementations of the elastic member are provided: a torsion spring and a compression spring. In other alternative implementations, the elastic member may also adopt other structures. For example, the compression spring in the second embodiment may be replaced with a spring plate an elastic pad, or the like. Alternatively, the elastic member may also be a tension spring connected between the inner side of the stopper and a position of the staple cartridge frame close to the second cutter groove, and in the first state, the biasing force of the tension spring to the stopper is a pulling force that pulls the first stop portion toward the inner side.

The foregoing content is a further detailed description of the present application with reference to specific preferred embodiments, and it cannot be determined that the specific implementation of the present application is limited to these descriptions. For a person of ordinary skill in the art to which this application belongs, several simple inferences or substitutions may still be made without departing from the inventive concept of the present application, and all of them should be regarded as falling within the protection scope of this application.

What is claimed is:

1. A staple head portion for a surgical stapler, comprising:

a first forceps holder and a second forceps holder arranged opposite to each other;

a connecting member that is connected to proximal end sides of the first forceps holder and the second forceps holder, the first forceps holder being rotatable relative to the connecting member;

a stopper rotatably mounted on the connecting member and comprising a first stop portion; and a firing mechanism movable along an axial direction of the surgical stapler and comprising a second stop portion; wherein the firing mechanism can be driven to move in a direction toward the distal end side, such that the first forceps holder rotates to be relatively closed with the second forceps holder; when the stopper is in a first state, the first stop portion is located on a path that the second stop portion moves in a direction toward a distal end side; and when the stopper is subjected to an external force of a driving member disposed on the first forceps holder to rotate relative to the connecting member in a first direction such that the first stop portion moves in a direction away from an axial center direction of the stapler, the stopper enters a second state, and the first stop portion disengages from the path that the second stop portion moves in the direction toward the distal end side, after the staple head portion is closed and the stopper enters the second state, the firing mechanism can be driven to continue moving in the direction toward the distal end side, so the normal firing of the surgical stapler is achieved.

2. The staple head portion according to claim 1, wherein a distal end of the connecting member is provided with a mounting portion for mounting the stopper; when the first forceps holder and the second forceps holder are in an open state, the mounting portion is at least partially located on a side of the second stop portion away from an axial center of the stapler; and the first stop portion and the second stop portion are provided with a first distance in the axial direction of the surgical stapler.

3. The staple head portion according to claim 2, wherein the stopper further comprises a pivoting portion rotatably mounted on the mounting portion via a pin shaft; and when the stopper is in the first state, the first stop portion protrudes toward the axial center direction of the stapler relative to the pivoting portion.

4. The staple head portion according to claim 3, further comprising an elastic member configured to apply a biasing force to the stopper to make the stopper rotate in a second direction opposite to the first direction.

5. The staple head portion according to claim 4, wherein the mounting portion is provided with a mounting groove opening toward the axial center direction of the stapler, and the stopper at least partially extends into the mounting groove.

6. The staple head portion according to claim 5, wherein the elastic member is a torsion spring disposed at the pin shaft.

7. The staple head portion according to claim 5, wherein the elastic member is a compression spring disposed between the stopper and an inner wall of the mounting groove.

8. The staple head portion according to claim 7, wherein a compression spring passage is provided inside the mounting groove, the compression spring is movably disposed in the compression spring passage, and the compression spring passage is arranged perpendicular to a side wall of the firing mechanism.

9. The staple head portion according to claim 8, wherein an axial width of the compression spring passage is greater than an axial width of the mounting groove.

10. The staple head portion according to claim 5, wherein the connecting member comprises a first limiting portion, and the stopper is provided with a second limiting portion; and the first limiting portion cooperates with the second limiting portion to limit a rotation angle of the connecting member in the second direction.

11. The staple head portion according to claim 5, wherein the connecting member further comprises a third limiting portion, and the stopper comprises a fourth limiting portion; and the third limiting portion cooperates with the fourth limiting portion to limit a rotation angle of the connecting member in the first direction.

12. The staple head portion according to claim 2, wherein the driving member is movable along the axial direction of the stapler; and when the driving member is located at the proximal end side of the first forceps holder and the first forceps holder rotates to be relatively closed with the second forceps holder, the driving member abuts against the stopper and drives the stopper to enter the second state from the first state.

13. The staple head portion according to claim 12, wherein when the stopper enters the second state from the first state, the firing mechanism moves a second distance in the direction toward the distal end side, and the first distance is greater than the second distance.

14. The staple head portion according to claim 12, wherein when the stopper enters the second state from the first state, the firing mechanism moves a second distance in the direction toward the distal end side, and the first distance is equal to the second distance.

15. The staple head portion according to claim 12, wherein a first driving portion is provided on a proximal end side of the driving member, and a second driving portion cooperating with the first driving portion is provided on a side of the stopper facing toward the axial center of the stapler.

16. The staple head portion according to claim 15, wherein two opposite sides of the first driving portion and the second driving portion are provided with a first guiding surface and a second guiding surface, respectively.

17. The staple head portion according to claim 16, wherein the first stop portion and the second driving portion are integrally formed; and when the stopper is in the first state, a side of the first stop portion facing toward the first forceps holder is the second guiding surface.

18. The staple head portion according to claim 1, wherein the firing mechanism comprises a cutter and a cutter push rod, a distal end of the cutter is provided with the second stop portion, and a proximal end of the cutter is connected to the cutter push rod.

19. The staple head portion according to claim 18, wherein when the stopper is in the second state and the firing mechanism moves in the direction toward the distal end side, the stopper at least partially abuts against a side surface of the cutter push rod to be maintained in the second state.

20. A surgical stapler, comprising the staple head portion according to claim 1.

* * * * *